(12) United States Patent
Steel et al.

(10) Patent No.: US 10,758,680 B2
(45) Date of Patent: Sep. 1, 2020

(54) DOSING MECHANISM AND DRUG DELIVERY DEVICE

(71) Applicant: SANOFI-AVENTIS DEUTSCHLAND GMBH, Frankfurt am Main (DE)

(72) Inventors: Samuel Steel, Leamington Spa (GB); Richard James Vincent Avery, Mickelton (GB); Anthony Paul Morris, Coventry (GB); Barry Yates, Cincinnati, OH (US); Matthew Meredith Jones, Warwick (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 15 days.

(21) Appl. No.: 15/568,106

(22) PCT Filed: Apr. 15, 2016

(86) PCT No.: PCT/EP2016/058322
§ 371 (c)(1),
(2) Date: Oct. 20, 2017

(87) PCT Pub. No.: WO2016/169845
PCT Pub. Date: Oct. 27, 2016

(65) Prior Publication Data
US 2018/0085528 A1    Mar. 29, 2018

(30) Foreign Application Priority Data
Apr. 21, 2015 (EP) .................................. 15164460

(51) Int. Cl.
*A61M 5/315* (2006.01)
*A61M 5/20* (2006.01)
*A61M 5/31* (2006.01)

(52) U.S. Cl.
CPC .......... *A61M 5/31553* (2013.01); *A61M 5/20* (2013.01); *A61M 5/2033* (2013.01);
(Continued)

(58) Field of Classification Search
CPC ........... A61M 2005/3126; A61M 2005/31518; A61M 2005/3154; A61M 2205/3306;
(Continued)

(56) References Cited

U.S. PATENT DOCUMENTS

2009/0292247 A1 * 11/2009 Basso .................. F04B 23/028
604/151
2013/0303836 A1 * 11/2013 Coble ................... A61F 5/0102
600/28

(Continued)

FOREIGN PATENT DOCUMENTS

| CA | 2838812 A1 * | 1/2013 | ........ A61M 5/31525 |
| CN | 1980705 | 6/2007 | |

(Continued)

OTHER PUBLICATIONS

International Preliminary Report on Patentability in International Application No. PCT/EP2016/058322, dated Apr. 21, 2015, 7 pages.
(Continued)

*Primary Examiner* — Nathan R Price
*Assistant Examiner* — Mark A Igel
(74) *Attorney, Agent, or Firm* — Fish & Richardson P.C.

(57) ABSTRACT

This disclosure refers to a dosing mechanism for use in a drug delivery device implementing a dialing mode and a dispensing mode, wherein the dosing mechanism comprises a dose button, a housing and a determination unit. The dose button is activatable by the user for dose dispense, causing displacement of an indicating element connected to the housing from a first position to a second position. The determination unit is adapted such that it detects the indi- (Continued)

cating element in its second position and thereby determines that the dosing mechanism is in the dispensing mode. With some embodiments, it is possible to distinguish between the dialing mode and the dispensing mode. Some embodiments further refer to a drug delivery device comprising the above dosing mechanism.

14 Claims, 14 Drawing Sheets

(52) U.S. Cl.
CPC ...... *A61M 5/3157* (2013.01); *A61M 5/31536* (2013.01); *A61M 5/31541* (2013.01); *A61M 5/31561* (2013.01); *A61M 5/31568* (2013.01); *A61M 5/31583* (2013.01); *A61M 5/31585* (2013.01); *A61M 2005/3126* (2013.01); *A61M 2005/3154* (2013.01); *A61M 2005/31518* (2013.01); *A61M 2205/3306* (2013.01); *A61M 2205/52* (2013.01); *A61M 2205/581* (2013.01); *A61M 2205/583* (2013.01)

(58) Field of Classification Search
CPC ........ A61M 2205/52; A61M 2205/581; A61M 2205/583; A61M 5/20; A61M 5/31553; A61M 5/2033; A61M 5/31536; A61M 5/31541; A61M 5/31561; A61M 5/31568; A61M 5/3157; A61M 5/31583; A61M 5/31585; A61M 5/31551; A61M 5/31535; A61M 5/31543; A61M 5/3583; A61M 5/31578; A61M 5/31586; A61M 5/3155; A61M 5/31548; A61M 5/315
See application file for complete search history.

(56) References Cited

U.S. PATENT DOCUMENTS

| | | | | |
|---|---|---|---|---|
| 2014/0128843 A1* | 5/2014 | Baker | ............... | A61M 5/31578 604/506 |
| 2014/0142512 A1* | 5/2014 | Butler | ............... | A61M 5/31585 604/189 |
| 2015/0005713 A1* | 1/2015 | Baran | ................ | A61B 5/14532 604/189 |
| 2015/0126963 A1* | 5/2015 | Despa | .................... | G16H 40/63 604/506 |

FOREIGN PATENT DOCUMENTS

| | | |
|---|---|---|
| CN | 102307611 | 1/2012 |
| CN | 103648552 | 3/2014 |
| CN | 103797336 | 5/2014 |
| CN | 104245020 | 12/2014 |
| JP | 2014-520615 | 8/2014 |
| JP | 2014-520617 | 8/2014 |
| WO | WO 2004/078241 | 9/2004 |
| WO | WO 2006/003130 | 1/2006 |
| WO | WO 2010/088973 | 8/2010 |
| WO | WO 2013/010887 | 1/2013 |
| WO | WO 2013/010893 | 1/2013 |
| WO | WO 2013/120778 | 8/2013 |
| WO | WO-2013120774 A1 * | 8/2013 |
| WO | WO 2014/118107 | 8/2014 |

OTHER PUBLICATIONS

International Search Report and Written Opinion in International Application No. PCT/EP2016/058322, dated Jul. 26, 2016, 10 pages.

* cited by examiner

Fig. 4a
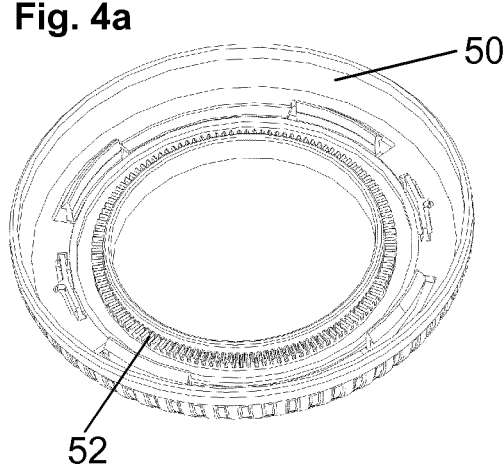
Fig. 4b
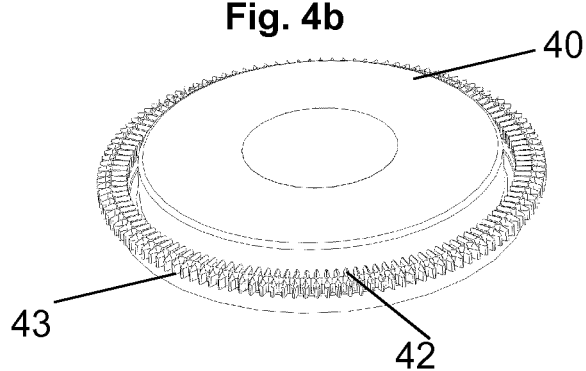
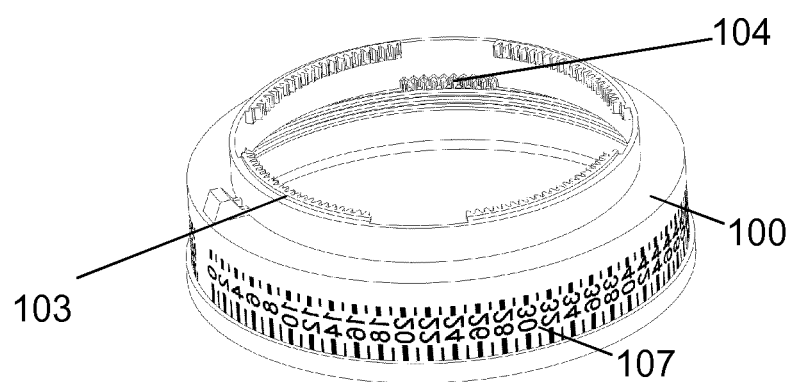
Fig. 4c

DOSING MECHANISM AND DRUG DELIVERY DEVICE

CROSS REFERENCE WITH RELATED APPLICATIONS

This application is a U.S. national stage application under 35 USC § 371 of International Application No. PCT/EP2016/058322, filed on Apr. 15, 2016, which claims priority to European Patent Application No. 15164460.6, filed on Apr. 21, 2015, the entire contents of which are incorporated herein by reference.

TECHNICAL FIELD

The present disclosure is generally directed to a dosing mechanism for use in a drug delivery device, i.e. a handheld injection device for selecting and dispensing a number of user variable doses of a medicament, and a respective drug delivery device.

BACKGROUND

Drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament.

There are basically two types of drug delivery devices: resettable devices (i.e., reusable) and non-resettable (i.e., disposable). For example, disposable drug delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism.

A further differentiation of drug delivery device types refers to the dosing or drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting. Further types of energy storage may comprise compressed fluids or electrically driven devices with a battery or the like.

These types of delivery devices generally comprise of three primary elements: a cartridge section that includes a cartridge often contained within a housing or holder; a needle assembly connected to one end of the cartridge section; and a dosing section with the dosing mechanism connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge section, a dose is set, and then the set dose is administered using the dosing mechanism of the dosing section. Removable needle assemblies may be threaded onto, or pushed (i.e., snapped) onto the pierceable seal end of the cartridge assembly.

The dosing section or dosing mechanism is typically the portion of the device that is used to set (select) a dose. During an injection, a plunger or piston rod contained within the dosing mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

The dosing section of drug delivery devices for selecting and dispensing a number of user variable doses of a medicament often comprises a display for indicating the selected dose to a user. This is especially important where a user may select a different dose each time depending on the state of health. There are mechanical displays, e.g. a drum with printed numbers on its outer surface, wherein the number corresponding to the actually selected dose is visible through a window or opening in the device.

A disposable drug delivery device is known from WO 2004/078241 A1, wherein the display comprises a number sleeve with numbers printed on its outer surface. The device further comprises a housing, a cartridge holder for retaining a cartridge containing a medicament, a piston rod displaceable relative to the cartridge holder, a driver coupled to the piston rod, a dose setting knob coupled to the driver and fixed to the number sleeve, and an injection button. The number sleeve is in threaded engagement with the housing, such that the number sleeve rotates along a helical path in a first direction during dose selecting and rotates back into the housing in a second, opposite direction during dose dispensing.

SUMMARY

Some embodiments implement a dialing mode and a dispensing mode, and comprise a dose button, a housing and a determination unit, wherein the dose button is activatable by the user for dose dispense causing displacement of an indicating element connected to the housing from a first position to a second position, wherein the determination unit is adapted such that it detects the indicating element in its second position and thereby estimates that the dosing mechanism is in the dispensing mode. Preferably, the determination unit is adapted not only to detect the change of position and the second position, but also the first position of the indicating element. The dose button is adapted such that it can be pressed by the user in order to be activated, i.e. to dispense a dose, and operably coupled to the indicating element.

The determination unit of the inventive dosing mechanism allows to distinguish between the dialing and the dispensing mode and thereby to distinguish between dialing down and dispensing when the dose display decrements. Preferably, the determination unit comprises a data processing unit, e.g. a microprocessor. The determination unit is preferably a part of an electronic module. In a preferred embodiment the electronic module is releasably attached to the housing of the dosing mechanism or drug delivery device by a snap fit connection. The determination unit further comprises preferably a proximity sensor and a lighting element in the visible or invisible wavelength range, for example a visible LED or an infrared LED.

The inventive dosing mechanism is in the dialing mode in which the dose button is not activated. In the dialing mode the user may dial up or down to increase or decrease the set dose. In contrast, in the dispensing mode the dosing mechanism facilitates dispensing of the dialed dose through a needle from a cartridge of the drug delivery device.

In a preferred embodiment the dosing mechanism comprises the indicating element which is connected to the housing, wherein the indicating element is the tip of a lever arm, preferably rigidly connected to the lever arm, wherein the lever arm is biased against displacement from the first position to the second position and connected or attached to the housing. Preferably, as the tip of the lever arm is rigidly connected to the lever arm, the first position of the lever arm corresponds to the first position of the tip and the second position of the lever arm corresponds to the second position of its tip. Further preferred the lever arm is a flexible lever making up part of the housing, which deflects under the load from a mechanism part moved by the dose button or the dose button into its second position and springs back to its first position wherein the tip is also in the first position when the dose button is released. Preferably, the lever arm may be rotated or pivoted or tilted around an axis extending through the attachment point or area where it is connected to the housing and/or deflected or moved from the first position to the second position when the dose button is activated In a further preferred embodiment for detecting that the indicating element is in its second position the determination unit comprises the proximity sensor adapted to detect this position using electromagnetic radiation provided by a lighting element emitting light of the visible and/or invisible wavelength range, e.g. a visible LED or an infrared LED, into the direction of the indicating element, wherein the proximity sensor detects the position of the indicating element measuring the reflected electromagnetic radiation by the indicating element and/or the absorption of the electromagnetic radiation impinging on the indicating element. The infrared LED illuminates inside the dosing mechanism through a light tube into a direction in which the position change of the indicating element can be safely detected.

The tip of the lever arm may comprise either a light or a dark surface which either reflects the impinged electromagnetic radiation or absorbs it, so that the position change of the indicating element from the first position to the second position is detected by a clear change in back reflected electromagnetic radiation.

In another preferred embodiment, the dosing mechanism comprises a transparent prism guiding the electromagnetic radiation from the proximity sensor of the determination unit to the indicating element. Accordingly, the transparent prism is accommodated between the proximity sensor and the indicating element. The prism thereby is transparent to the electromagnetic radiation provided by the lighting element and detected by the proximity sensor. Usually, the electromagnetic radiation comprises a waveband of the visible light, the infrared light and/or UV light. Accordingly, the prism is transparent to the electromagnetic radiation of the used waveband.

In a further improved embodiment, the determination unit comprises a display, preferably attached to the housing, which is adapted to visibly and/or audibly display whether the dosing mechanism is in the dialing mode or in the dispensing mode. Therefore, the proximity sensor sends a respective signal to the display containing the mode information. For an audible display the display comprises a loudspeaker for example. This is an advantage for the user because then the user knows exactly whether the dosing mechanism or the drug delivery device comprising the dosing mechanism is in the dialing or dispensing mode.

It is further preferred if the determination unit further comprises a sensor, preferably a camera, reading the dialed dose and/or the dispensed dose. Accordingly, the display may visually and/or audibly display also the dialed and/or dispensed dose. Thereby, it is possible to for example enlarge the display with regard the mechanical display of a conventional drug delivery device and to show the doses to visually impaired persons.

In another embodiment, the determination unit comprises a storage unit storing the read dialed doses and/or the red dispensed doses for further data processing.

In another embodiment, the dosing mechanism comprises a drive gear coupled to the dose button, wherein activation of the dose button means movement of the dose button in an axial direction relative to the housing thereby driving the drive gear in the axial direction relative to the housing which causes displacement of the indicating element from the first position to the second position, for example by applying a load to a protrusion of the lever arm containing the indicating element as the lever arm tip. Alternatively, the drive gear may comprise a protrusion which applies a load to the lever arm with the tip as indicating element in order to cause its displacement from the first position to the second position. This embodiment comprises a very easy and cost effective implementation of a dosing mechanism with determination of the kind of mode.

An assembly comprising the dosing mechanism described above, wherein the determination unit is accommodated within a separate module that is releasably attached to the dosing mechanism, may improve visualization of the dialed dose. Analogously, an assembly comprising a drug delivery device with the above described dosing mechanism, wherein the determination unit is accommodated in a separate module that is releasably attached to the drug delivery device, may improve visualization of the dialed dose. The assemblies in which the determination unit is accommodated within a separate module have the advantage that the module can be reused with different disposable dosing mechanisms or drug delivery devices. As the module comprising the determination unit is an electronic module which is costlier it makes sense to reuse such a device.

Preferably, the module is an electronic module separate from the drug delivery device or dosing mechanism, further comprising a power source for delivery of electrical energy to the proximity sensor, the lighting element, the storage unit and/or the display, for example a battery.

For attachment to the dosing mechanism or the drug delivery device the module comprises attachment means which may be connected to according attachment means of the dosing mechanism or the drug delivery device releasably or non-releasably, e.g. corresponding snap-fit connection means.

The drug delivery device usually comprises a cartridge, wherein preferably, in a reusable drug delivery device the cartridge may be replaceable.

The cartridge of the drug delivery device typically contains a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6NH2,
H-(Lys)6-des Pro36, Pro37, Pro38 [Trp(O2)25, Asp28] Exendin-4(1-39)-(Lys)6NH2,
H-Asn-(Glu)5-des Pro36, Pro37, Pro38 [Trp(O2)25, Asp28] Exendin-4(1-39)-(Lys)6NH2,
H-(Lys)6-des Pro36 [Met(O)14, Asp28] Exendin-4(1-39)-Lys6NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6NH2,
H-(Lys)6-des Pro36, Pro37, Pro38 [Met(O)14, Asp28] Exendin-4(1-39)-(Lys)6NH2,
H-Asn-(Glu)5 des Pro36, Pro37, Pro38 [Met(O)14, Asp28] Exendin-4(1-39)-(Lys)6NH2,
H-Lys6-des Pro36 [Met(O)14, Trp(O2)25, Asp28] Exendin-4(1-39)-Lys6NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6NH2,
H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra-low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by γ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Some embodiments are not directed to so called fixed dose devices which only allow dispensing of a predefined dose without the possibility to increase or decrease the set dose.

Some embodiments are, in general, applicable for both disposable devices as well as for reusable devices.

Some embodiments may advantageously allow electronic processing of data provided by the dosing mechanism or drug delivery device, such as dialed doses or the dispensed doses and further, to improve visualization of the dialed dose.

Exemplary embodiments will now be described in further detail with reference to the accompanying schematic drawings, wherein

BRIEF DESCRIPTION OF THE FIGURES

FIGS. 4a-c perspective views of different components of the embodiment of FIG. 1;

DETAILED DESCRIPTION

Figure 1:
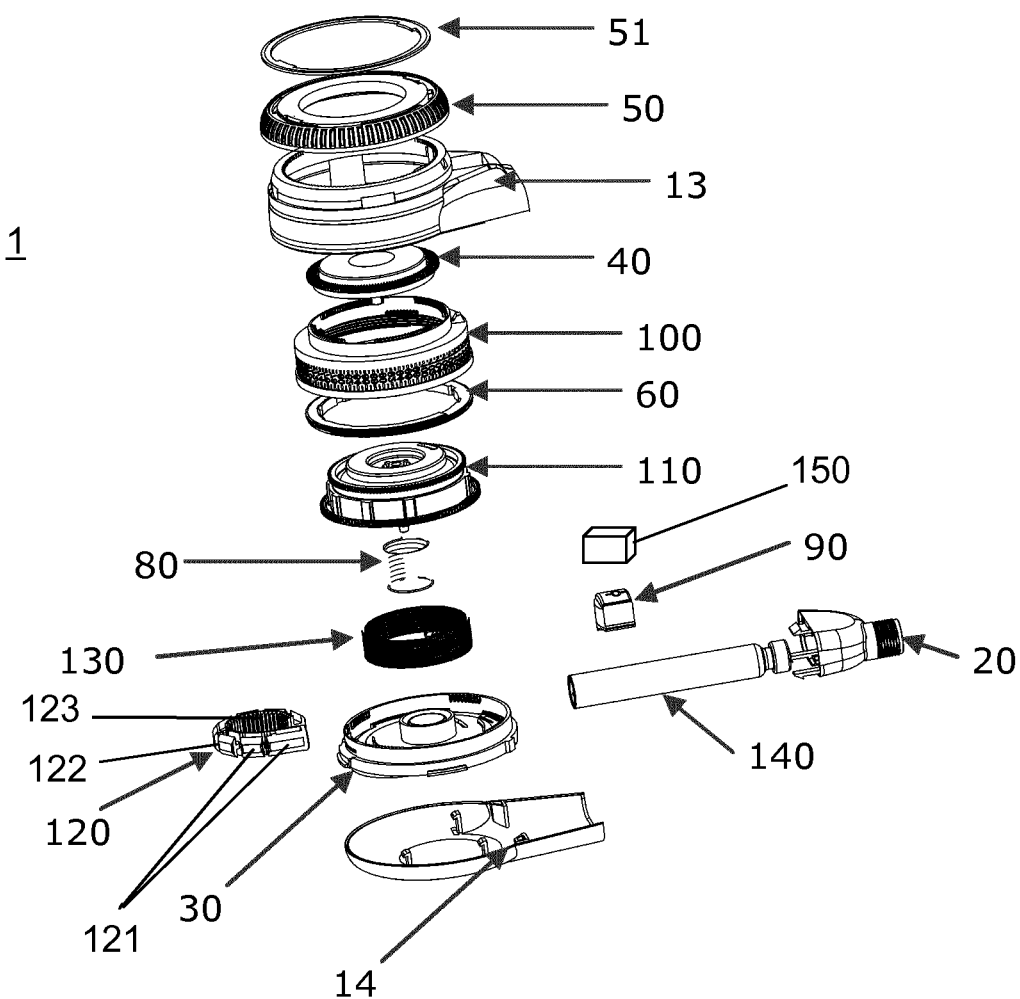
FIG. 1 shows an exploded view of a first embodiment of a drug delivery device comprising a dosing mechanism.
Figure 2:
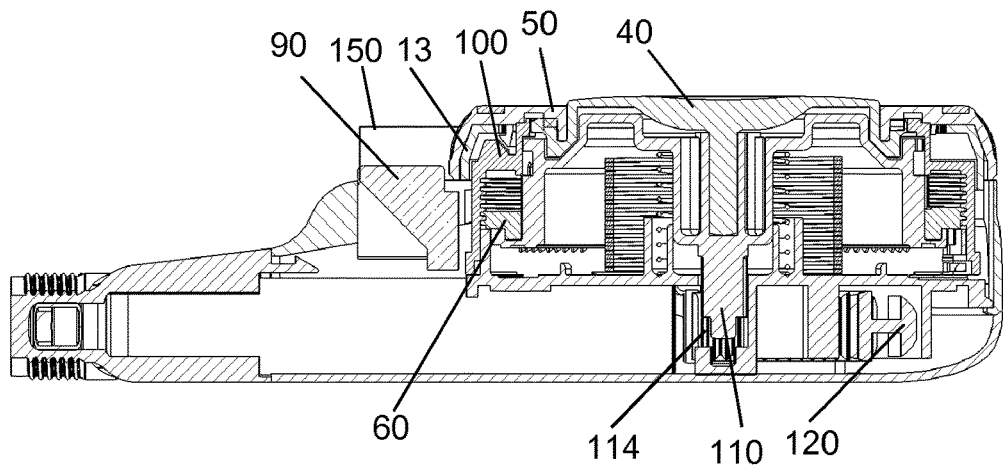
FIG. 2 a cut view of the embodiment of FIG. 1.

FIGS. 1 and 2 show views of the drug delivery device 1, wherein FIG. 1 illustrates the component parts incorporated into the drug delivery device 1 which are a casework 10 or body with an upper or outer casework 13 and a lower casework 14, a cartridge holder 20, a base element or chassis 30, a trigger or dose button 40, a dose setting or dial member 50 with a dial cover 51, a last dose nut 60, a trigger spring 80, a prism 90, a setting element or number wheel 100, a drive gear 110, a flexible piston rod 120, a drive spring 130, a medicament cartridge 140 and a first module 150. The dial cover 51 is rigidly fixed into the dial member 50. The upper casework 13, the lower casework 14 and the chassis 30 are rigidly connected to each other and form together the body or housing 10. The upper casework 12 has an opening into which prism 90 is inserted and permanently fixed. Chassis 30 comprises a bearing, which may have the form of a cut open cylinder located at the center of chassis 30, for receiving the pinion 114 of the drive gear 110.

As shown in FIG. 2, the button 40 is axially constrained between the dial member 50 and drive gear 110. The number wheel 100 is axially constrained between the chassis 30 and the upper casework 13. It is free to rotate, relative to the upper casework 13, between two fixed, rotational stops formed by abutments on the number wheel 100 and the upper casework 13.

As the detailed views in FIGS. 4a to 4c of the dial member 50 (FIG. 4a), the button 40 (FIG. 4b) and the number wheel 100 (FIG. 4c) show, the button 40 has inner spline/tooth features 42 that interface with corresponding inner spline/tooth features 52 on an inner surface of the dial member 50 and spline/tooth features 43 that interface with corresponding spline/tooth features 103 on a radial inner surface of the number wheel 100. These interfaces disconnect during dose delivery. The dial member 50 is axially constrained to the body 10 via retention features (not shown) and is further rotationally constrained, via the splined/tooth interface 52/42, to the button 40 during dose selection. The spline features 103 of the number wheel 100 interact with the button 40 during dialing. Further, on an inner surface, the number wheel 100 also has spline/tooth features 104 that interact with the corresponding drive features of the drive gear 110 during dispense. On the outer circumferential surface, the number wheel 100 is provided with markings (e.g. numbers) 107 that indicate the set dose.

The drive spring 130 is provided in the form of a helical torsion spring and is attached at one end to the chassis 30 and at the other end to the drive gear 110. The drive spring 130 is charged for life, which means that the drive spring is fully charged during assembly and does not require charging by the user until the entire contents of the cartridge 140 is dispensed.

The drive gear 110 is axially constrained between the chassis 30 and number wheel 100 and biased away from the chassis 30 by the trigger spring 80 that is provided in the form of a compression spring. It travels axially with the button 40 when the button 40 is pressed to commence dose delivery. During dose dialing or selection, the drive gear 110 is in splined engagement with the chassis 30 and hence locked against rotation, but when it travels axially as the button 40 is depressed downwardly for dose delivery this spline engagement is disconnected. Similarly, the separate spline features between the number wheel 100 and the drive gear 110 are engaged when the button 40 is depressed. The trigger spring 80 applies a force between the chassis 30 and drive gear 110 to separate them. In an "at rest" condition, prior to pressing the button 40, this ensures that the drive gear 110 is rotationally coupled to the chassis 30 and that the button splines 42 are engaged with the dial member 50.

The flexible piston rod 120 is located within the chassis 30 and is engaged with the drive gear 110 via a rack and pinion interface so that counter-clockwise (CCW) rotation of the drive gear 110 advances the flexible piston rod 120 towards a bung in the cartridge 140. The pinion 114 is rotatably held in the chassis 30 and is in meshed engagement with the piston rod 120. The piston rod 120 is a single component with discrete rigid rod pieces or segments 121 (see FIG. 1) connected together by thin sections of material which form flexible hinges 122. The end faces of the segments 121 are planar and, when the piston rod 120 is straightened the adjacent segment faces abut each other, allowing the component to withstand a compressive load. Each segment 121 is shaped as a flat plate provided with rack teeth 123 on one side and a flange on the opposite side. The segment 121 facing towards the cartridge 140 comprises a pressure foot for contacting the cartridge bung. As the piston rod 120 is advanced, via the rack 123 and pinion 114 engagement with the drive gear 110, the trailing segments 121 of piston rod 120 are drawn into engagement with the drive gear pinion 114. The subsequent segments 121 drive the preceding segments, loading them in compression, and apply a force to the bung. As the piston rod 120 advances, the first segment moves out of a support provided by the chassis 30. Without additional support it is likely that the piston rod 120 would buckle under this compressive loading. The additional support to prevent buckling is created by the inner side wall of the cartridge 140 providing constraint to the outer surfaces of the piston rod 120.

The distal end of the flexible piston rod 120 acts on the bung within the liquid medicament cartridge 140. The liquid medicament cartridge 140 is housed within the cartridge holder 20. The cartridge holder 20, chassis 30, outer/upper casework 13, lower casework 14, and the prism 90 are fixed rigidly relative to one another.

The drug delivery device can be operated to deliver a number of user variable doses of medicament from the cartridge 140, via a needle (not shown). The device as shown in FIG. 1 is disposable and is delivered to the user in a fully assembled condition ready for use. The mechanism provides separate user interfaces for setting and delivery of a dose. In short, a dose is set by rotating dial member 50 located on the face of the device. Delivery of a dose is initiated by pressing dose button 40, positioned in the center of the dial member 50, and dose delivery will continue while the dose button 40 remains depressed, until the complete set dose has been delivered. The mechanism provides audible, visual and tactile feedback, during the setting and delivery of each dose. Any dose size can be selected between zero and a pre-defined maximum, in increments to suit the medicament and user profile. The mechanism permits cancelling of a dose without any medicament being dispensed by rotation of the dial member 50 in the opposing direction to when selecting a dose.

The force required to actuate the dose button 40 and the distance which it has to move are small, providing a significant ergonomic advantage, particularly for those users with impaired dexterity. The mechanism requires consistent user input forces to set a dose and initiate the delivery of a dose, which are insensitive to variations in the force required to displace the bung within the cartridge 140. The dial member 50 is disengaged during dose delivery so that it does not rotate, which improves handling of the device during use. The device has relatively low part count, very compact size and is particularly attractive for cost sensitive device applications.

In the following use and function of the device will be described in more detail.

Figure 3:
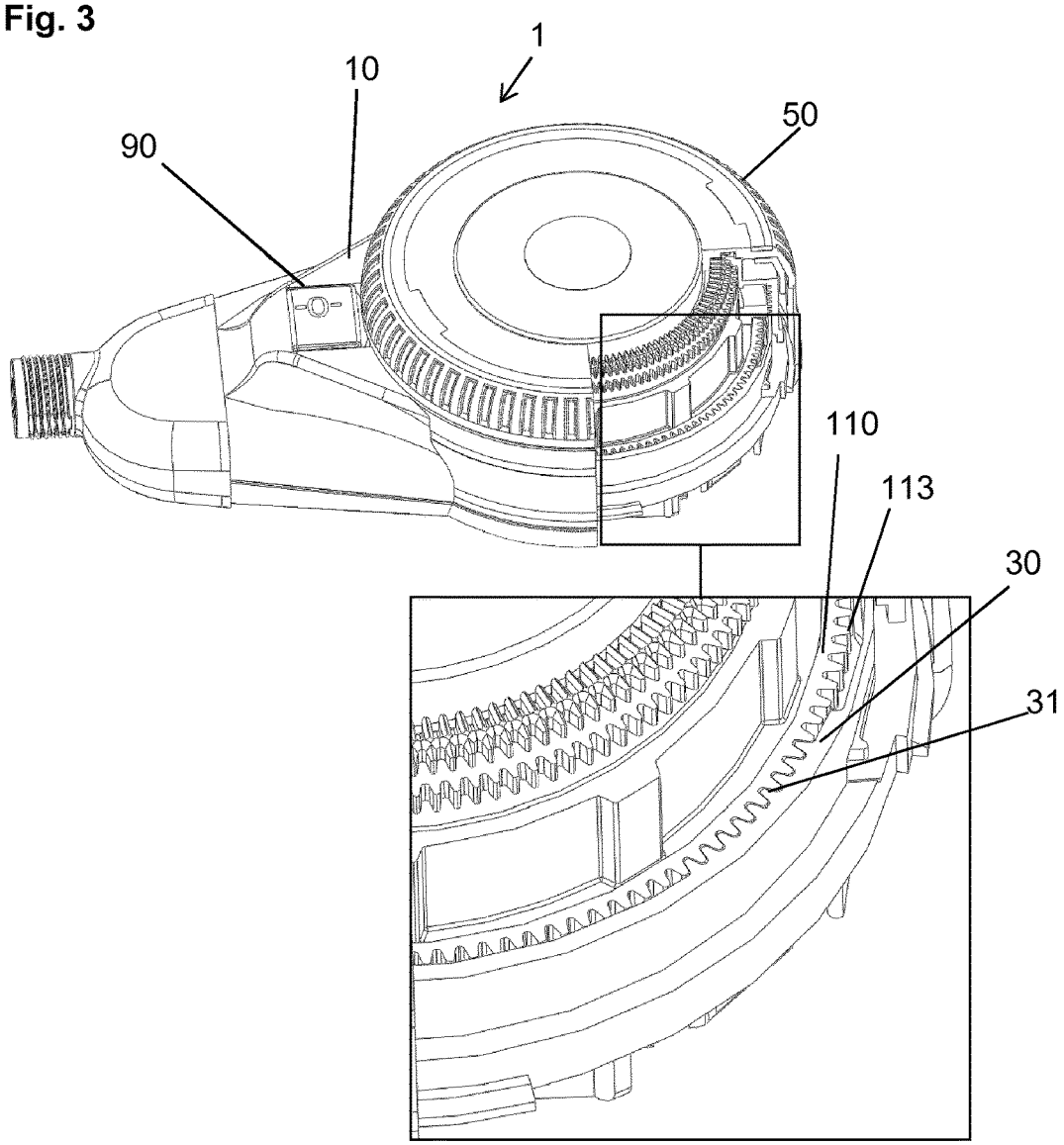
FIG. 3 a perspective view of the embodiment of FIG. 1 with parts removed.

FIG. 3 shows the device 1 in the 'at rest' condition. Dose marking '0' on the number wheel is visible through the prism 90. The drive spring, which is fully charged during assembly of the device or which is pre-wound, applies a torque to the drive gear 110 when zero dose units are dialed. The drive gear 110 is prevented from rotating, under the action of this torque, by a clutch mechanism formed by the spline interface with the chassis 30. As shown in the enlarged extract of FIG. 3, the splined interface comprises outer spline/tooth features 113 on an outer circumferential surface of the drive gear 110 that engage with inner spline/tooth features 31 on an inner circumferential surface of the chassis 30. By relative axial displacement, the drive gear 110 and the chassis 30 can be decoupled so that the drive gear 110 can rotate under the force of the drive spring.

Figure 5:
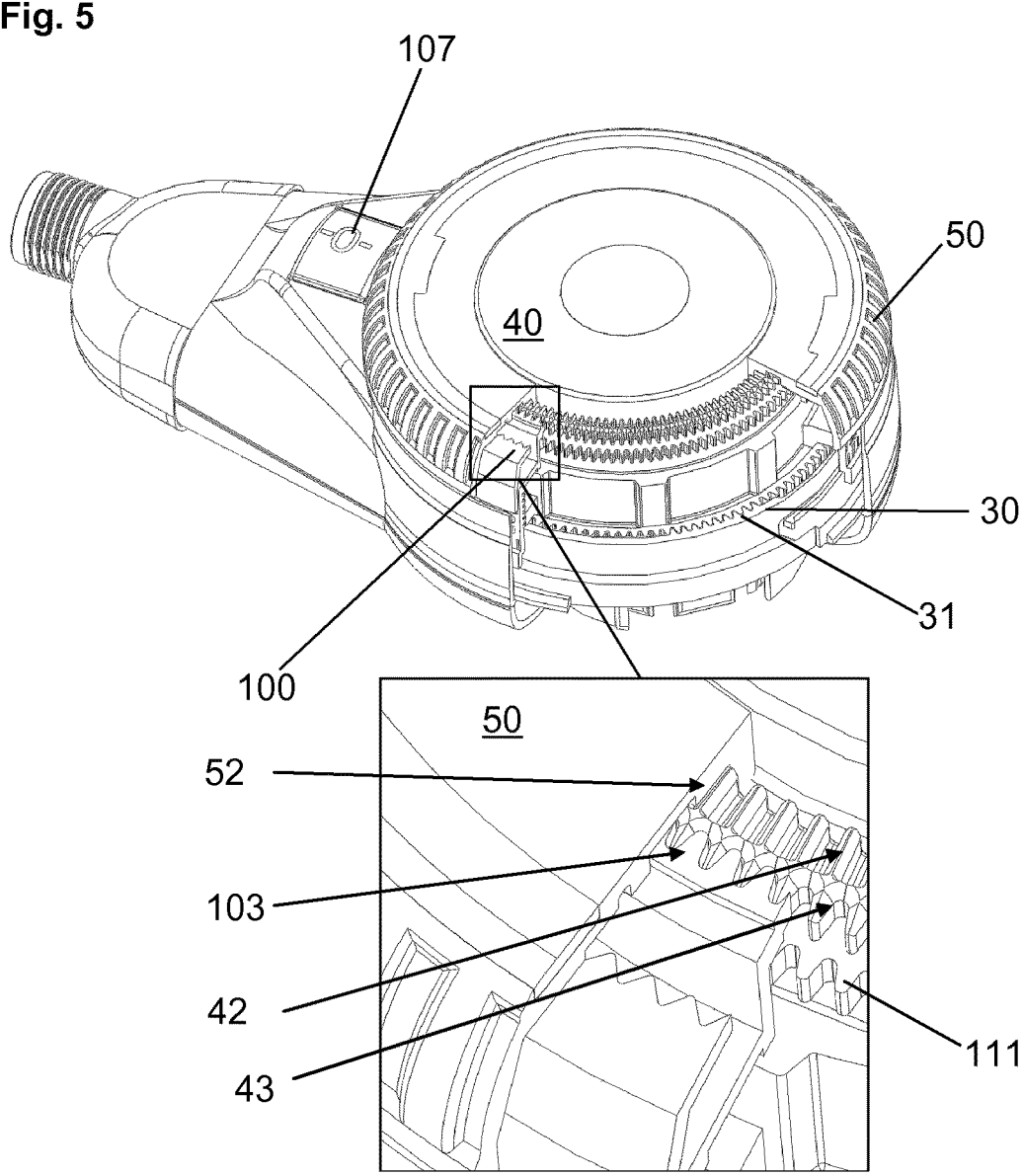
FIG. 5 a perspective view of the embodiment of FIG. 1 with parts removed.

To dial a variable dose of liquid medicament, the user rotates the dial member 50 in clockwise (CW) direction. The spline features 52 provided on the underside of the dial member 50, and spline features 42, 43 on the button 40 and spline features 103 the number wheel 100 are engaged (see FIG. 4). FIG. 5 shows the spline interfaces during dose dialing. As the enlarged section of FIG. 5 illustrates, rotation of the dial member 50 generates an identical rotation in the button 40 due to the spline interface 52/42 between the button 40 and the dial member 50. Further, because of the spline interface 43/103 between the button 40 and the number wheel 100, the number wheel 100 is also caused to rotate. The drive gear 110 is prevented from rotating due to the engagement of its splined teeth 113 with the splined teeth 31 of the chassis 30 being part of the fixed housing (see FIGS. 3 and 5).

Figure 6:
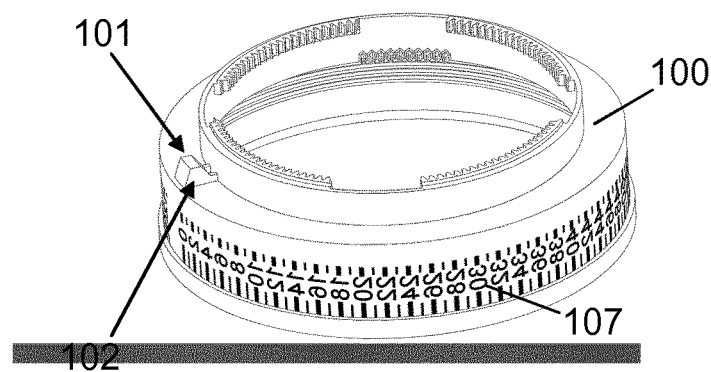
FIG. 6 a perspective view of the number wheel of the embodiment of FIG. 1.

As shown in FIG. 6, the number wheel 100 has two fixed rotational stops, namely a maximum dose stop 101 and a zero dose stop 102 formed by an abutment. On an inner surface of the upper casework 13, respective counter abutments are provided. CW rotation of the dial member 50 rotates the number wheel 100 away from a zero dose stop formed by said counter abutment on the casework 13 and towards a maximum dose stop formed as a counter abutment surface on the upper casing 13. The dial member 50 can be rotated by the user in both CW and CCW directions when the number wheel 100 is not in contact with the zero dose or maximum dos stop abutments in the casework 13. The zero dose stop 102 prevents CCW rotation of the dial member 50 below the zero-unit position. The maximum dose stop 101 prevents setting of a dose greater than the mechanism maximum.

Figure 7:
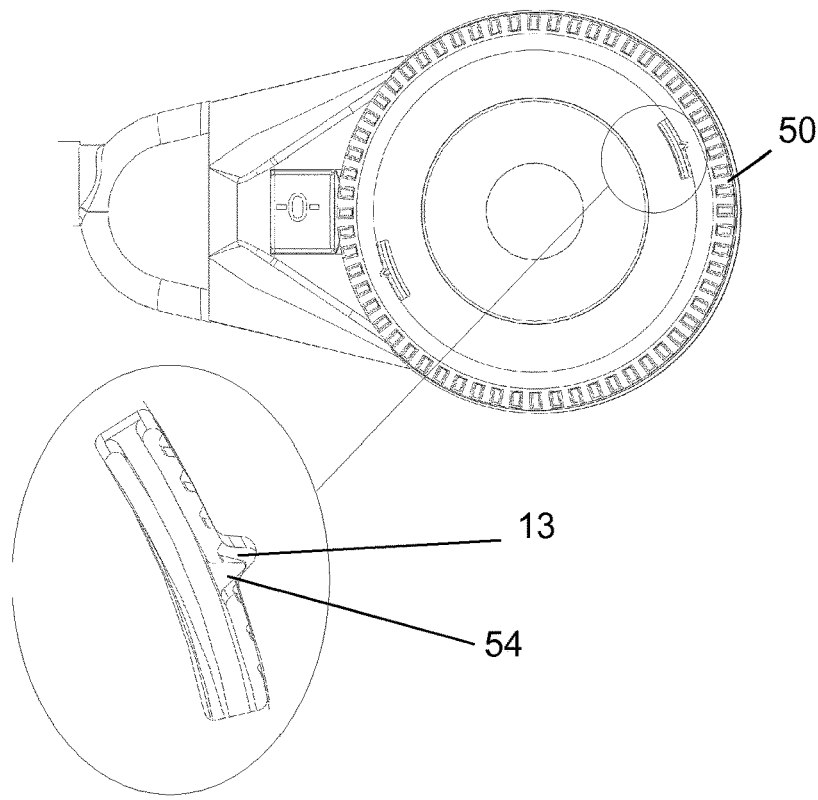
FIG. 7 a top view of the embodiment of FIG. 1.

In FIG. 7, a top view of the drive mechanism is shown, where the dial member 50 is provided with a dial clicker 54 in the form of a flexible arm that clicks against a series of protrusions on the upper casework 13. The clicker 54 is hidden from view of the user by the dial cap 51 which clips onto the dial 50. Since during dose delivery the dial member 50 does not move, the dial 54 clicker only operates during dialing of a dose. The dial clicker 54 biases the number wheel 100 relative to the prism 90 through the dial member 50 ensuring that only whole units of medicament are dialed.

Figure 8:
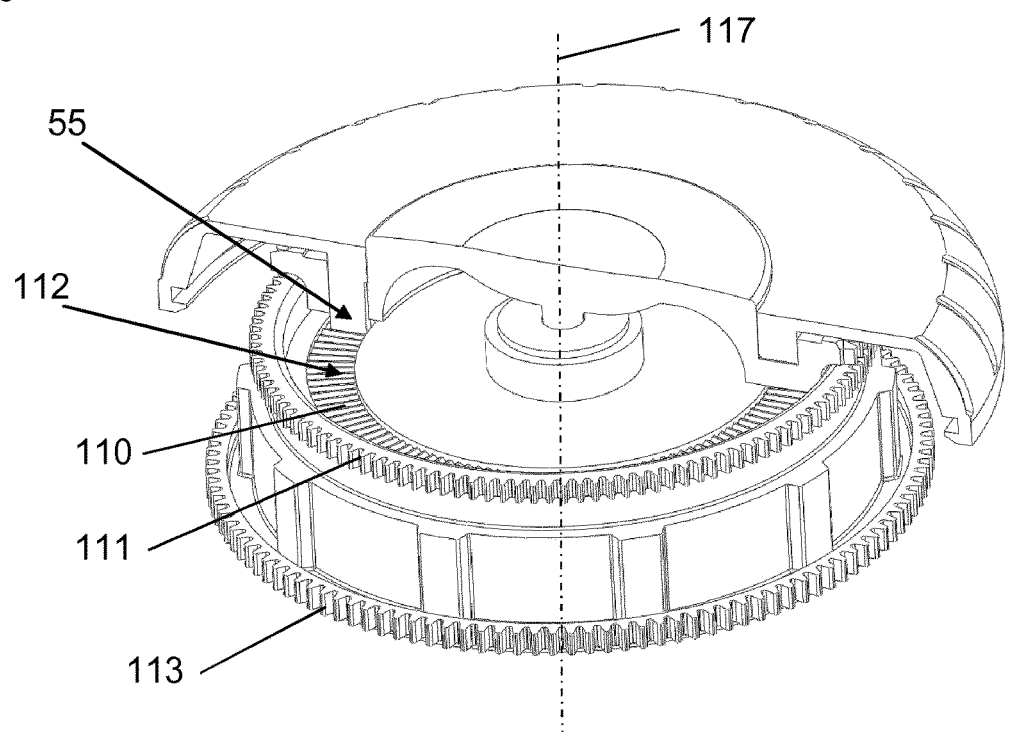
FIG. 8 a perspective view of parts of the dosing mechanism of a second embodiment.

In FIG. 8, an alternative of the clicker mechanism is presented. This clicker mechanism works axially between the dial member 50 and the drive gear 110. Radial teeth 112 accommodated on a helical surface on the drive gear 110 may react against a rigid clicker arm 55 on the dial member 50. As each unit is dialed by rotating the dial member 50 around the axis of rotation 110 of the drive gear 110, the drive gear is forced axially downwards by the depth of the teeth 112, and then returns to its original axial height under the action of the trigger spring. This causes the audible click as each unit is dialed. During delivery, the dial clicker 55 is disengaged through the axial travel of the button 40 and drive gear 110 moves away from the dial member 50. This embodiment is advantageous in terms of robustness as the metal spring is likely to be more robust than a plastic arm. In addition, multiple contact faces can be used to spread the load more evenly, reducing damage, without increasing the torque required to overcome the clicker. FIG. 8 also shows that the outer circumferential surface of the drive gear 110 is generally provided with the two sets of splined teeth 111 and 113, wherein the first set 111 is for engagement with correspondingly formed spline features 104 on the number wheel and wherein the second set 113 is provided for engagement with the chassis 30.

Figure 9:
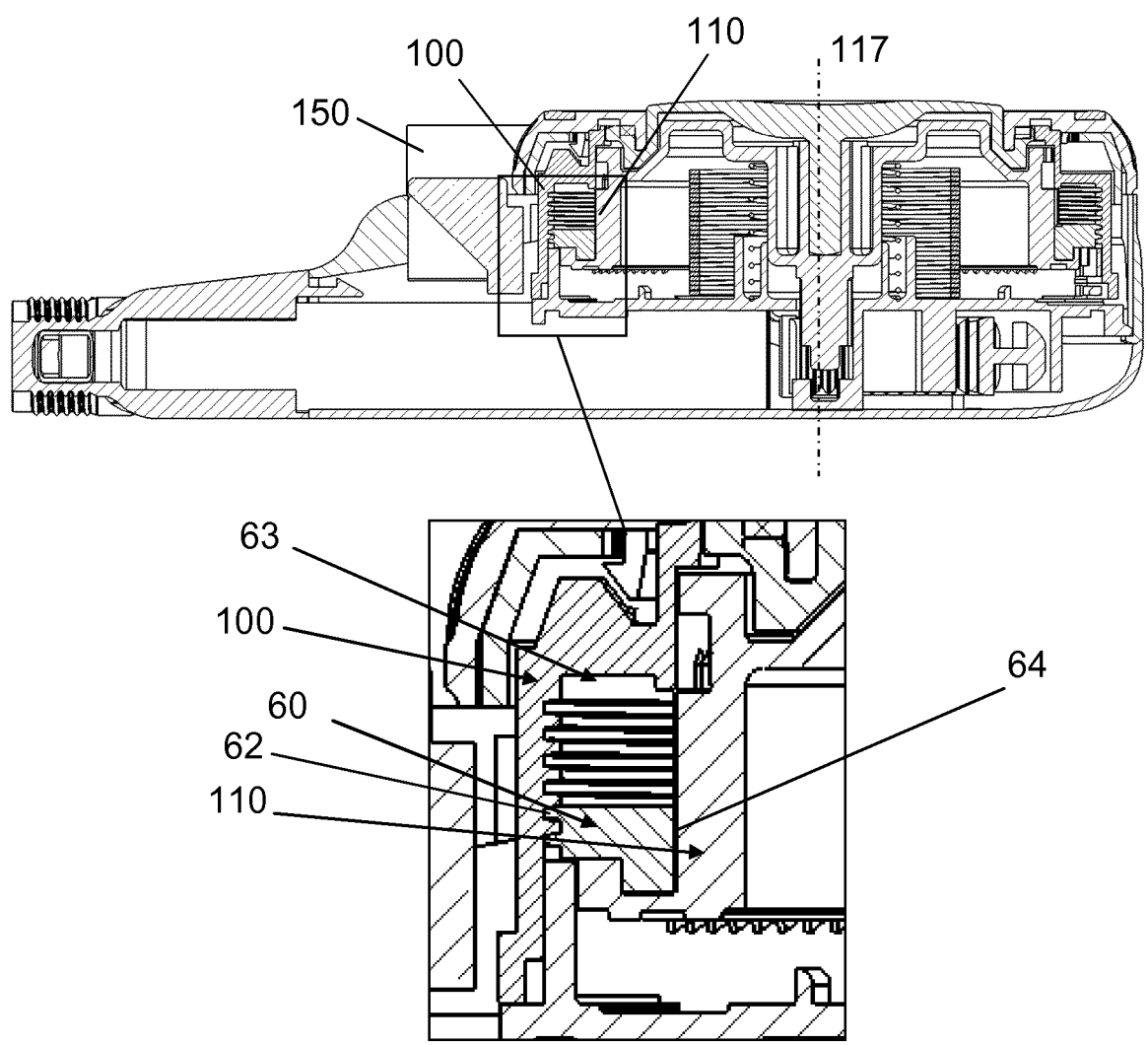
FIG. 9 the embodiment of FIG. 1 in a cut view.

With regard to FIG. 9, the last dose mechanism is discussed. The last dose nut 60 is located between the number wheel 100 and the drive gear 110. It is rotationally coupled to the drive gear 110 via a splined interface 64 provided on a radial inner surface of the last dose nut 60 and on a radial outer surface of the drive gear 110 that enables relative axial displacement but prevents relative rotation. For example, the splined interface 64 may include axially extending ribs on the radial inner surface of the last dose nut 60 that engage in respective axially extending grooves on the radial outer surface of the drive gear 110. Further, the last dose nut 60 is engaged with the number wheel 100 by a threaded engagement wherein the last dose nut is provided with a helically extending groove forming an outer thread 62 engaging a helically extending counterpart in the number wheel so that the last dose nut 60 moves along a helical path relative to the number wheel 100 when relative rotation occurs between the number wheel 100 and the drive gear 110 (i.e. during dialing). Relative rotation of the number wheel 100 and the drive gear 110 around the rotational axis 117 causes the last dose nut 60 to travel axially towards a last dose abutment (end stop, not shown) on the number wheel 100. Depending on how many units have already been delivered by the mechanism, during selection of a dose, the last dose nut 60 may contact its last dose abutment 105. The abutment prevents further relative rotation of the number wheel 100 and the drive gear 110, and therefore limits the dose that can be selected. The position of the last dose nut 60 is determined by the total number of relative rotations between the number wheel 100 and drive gear 110. The total number of relative rotations includes all rotations that have occurred each time the user sets a dose. With the mechanism in a state in which a dose has been selected, the user is able to deselect any number of units from this dose. Deselecting a dose is achieved by the user rotating the dial member 50 CCW. The relative rotation between the number wheel 100 and the drive gear 110 causes the last dose nut 60 to return axially, away from the last dose abutment.

Figure 10A:
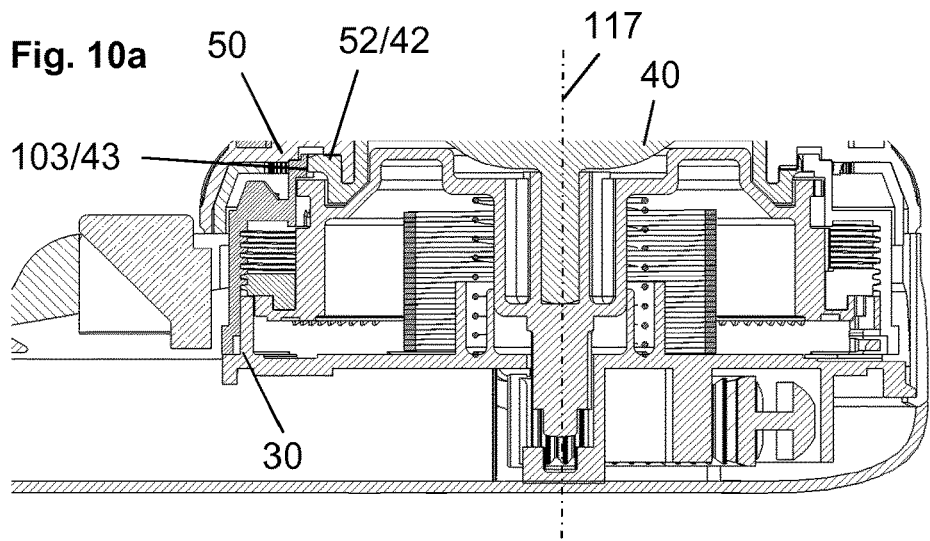
FIGS. 10a-c a dispense sequence of the dosing mechanism of the embodiment of FIG. 1 in a cut view.
Figure 10B:
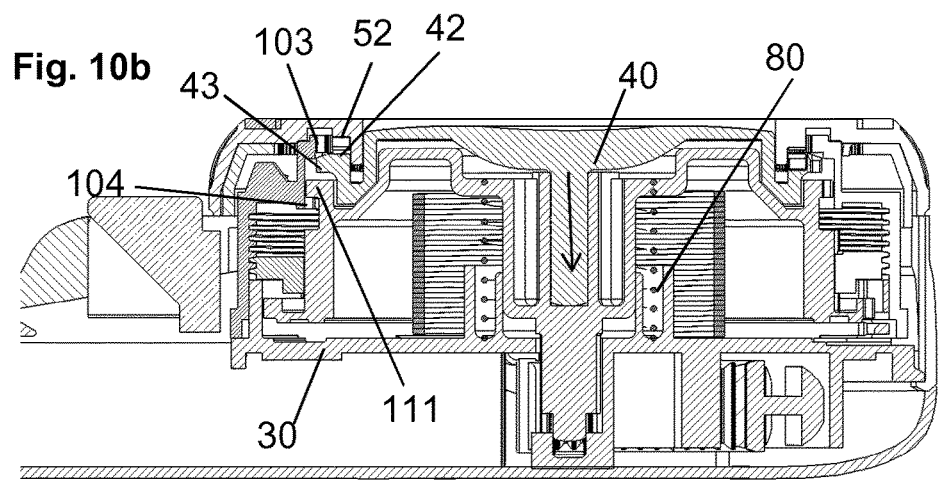
Figure 10C:
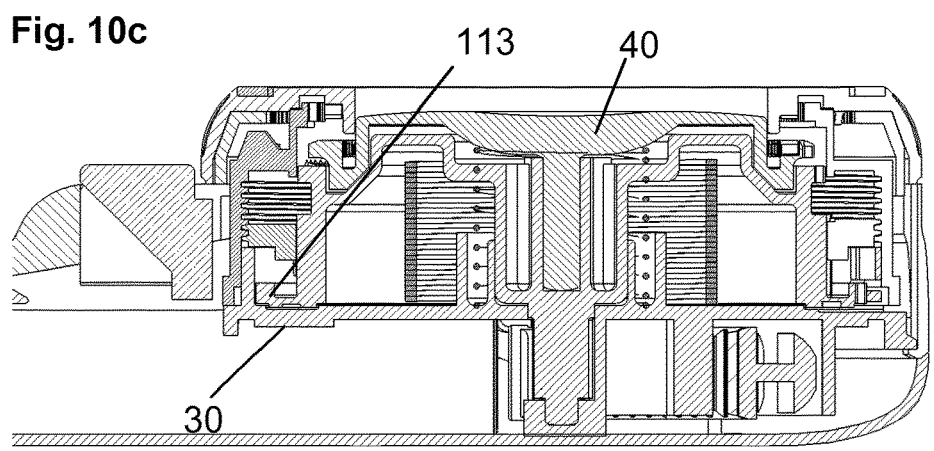

In FIGS. 10*a* to 10*c*, a sequence in the drive mechanism to dispense a dose is shown. FIG. 10*a* shows the device after a dose has been dialed. The zero dose stop 102 of the number wheel 100 has been rotated away from its counter-abutment. The button 40 is engaged with the number wheel 100 via the spline interface 43/103 and the dial member 50 is engaged with the button 40 via the spline interface 52/42.

When for dose dispense the button 40 is depressed in an axial direction along the axis of rotation 117, the button 40 moves relative to the dial member 50 and the number sleeve 100 so that the button 40 disengages from the spline features 52 of the dial member 50 and disengages from the spline features 103 of the number wheel 100.

The drive gear 110 moves axially with the button 40 against the force of the trigger spring 80, and when the button 40 is partially depressed (FIG. 10*b*), the drive gear 110 engages the splined teeth 111 on its outer circumferential surface with the spline features 104 on the number wheel 100. As the button is fully depressed (FIG. 10*c*), the drive gear 110 disengages from the chassis locking teeth or spline feature 31 and is now able to rotate relative to the chassis 30. In other words, the drive gear 110 is movable from a first 'at rest' position to a second actuated position where the drive gear is disengaged from the chassis 30.

After the button 40 is fully depressed, the drive gear 110 and the number wheel 100 are rotationally locked and free to rotate under the action of the drive spring 130. The button 40 is disengaged from all spline teeth and therefore the mechanism can rotate relative to the dose button 40 and the dial member 50.

The pinion 114 of the drive gear 110 acts on the teeth of the piston rod 120 causing the medicament to be dispensed. At the end of dose, the number wheel 100 zero stop abutment stops against the stop feature in the outer casework 13 causing the mechanism to stop. During delivery of a dose, the drive gear 110 and the number wheel 100 rotate together, so that no relative motion in the last dose nut 60 occurs.

The dose delivery clicker arm is a compliant cantilever arm integrated into the chassis 30, which interfaces axially with ratchet features on the drive gear 110 (not shown). The ratchet teeth spacing corresponds to the drive gear 110 rotation required to deliver a single dose unit. During dispense, as the drive gear 110 rotates, the ratchet features engage with the clicker arm to produce an audible click with each dose unit delivered.

When the button 40 is released, the trigger spring 80 causes the drive gear 110 and hence the button 40 to travel axially to their at-rest position. This travel causes the drive gear 110 spline teeth 113 to mesh with the chassis 30 again, locking the drive gear 110 against further rotation. The drive gear 110 also disengages its spline teeth 111 from the number wheel 100. The button 40 then re-engages its spline teeth features 42 and 43 with the dial member 50 and the number wheel 100. The user is then free to dial their next dose when required.

Figure 11:
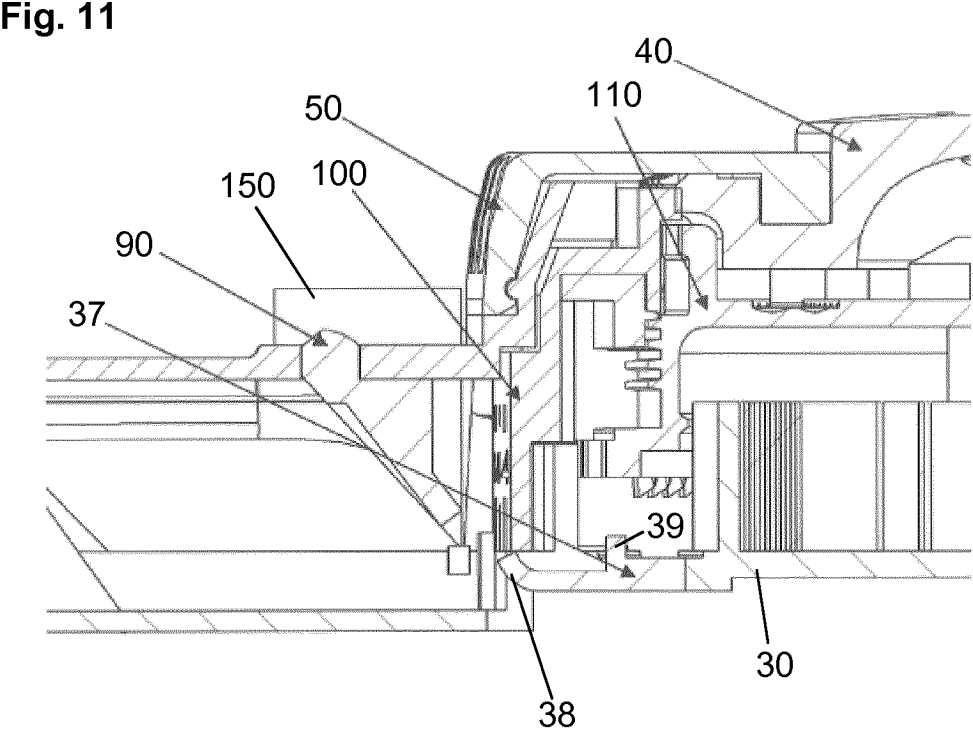
FIG. 11 a part of the cut view of the embodiment of FIG. 1 showing the indicating element.
Figure 12:
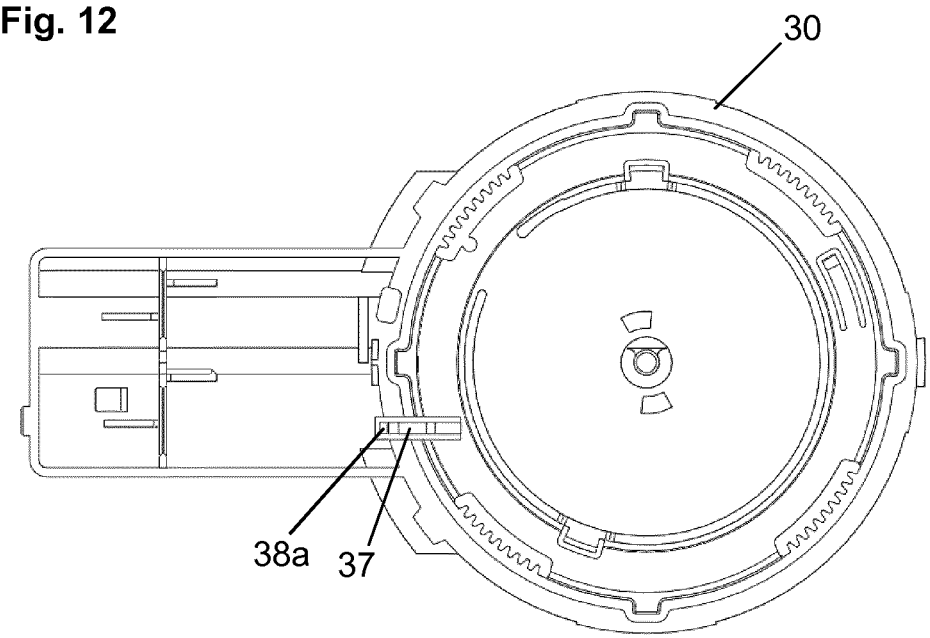
FIG. 12 a top view of the chassis (base element) of the embodiment of FIG. 1.
Figure 13:
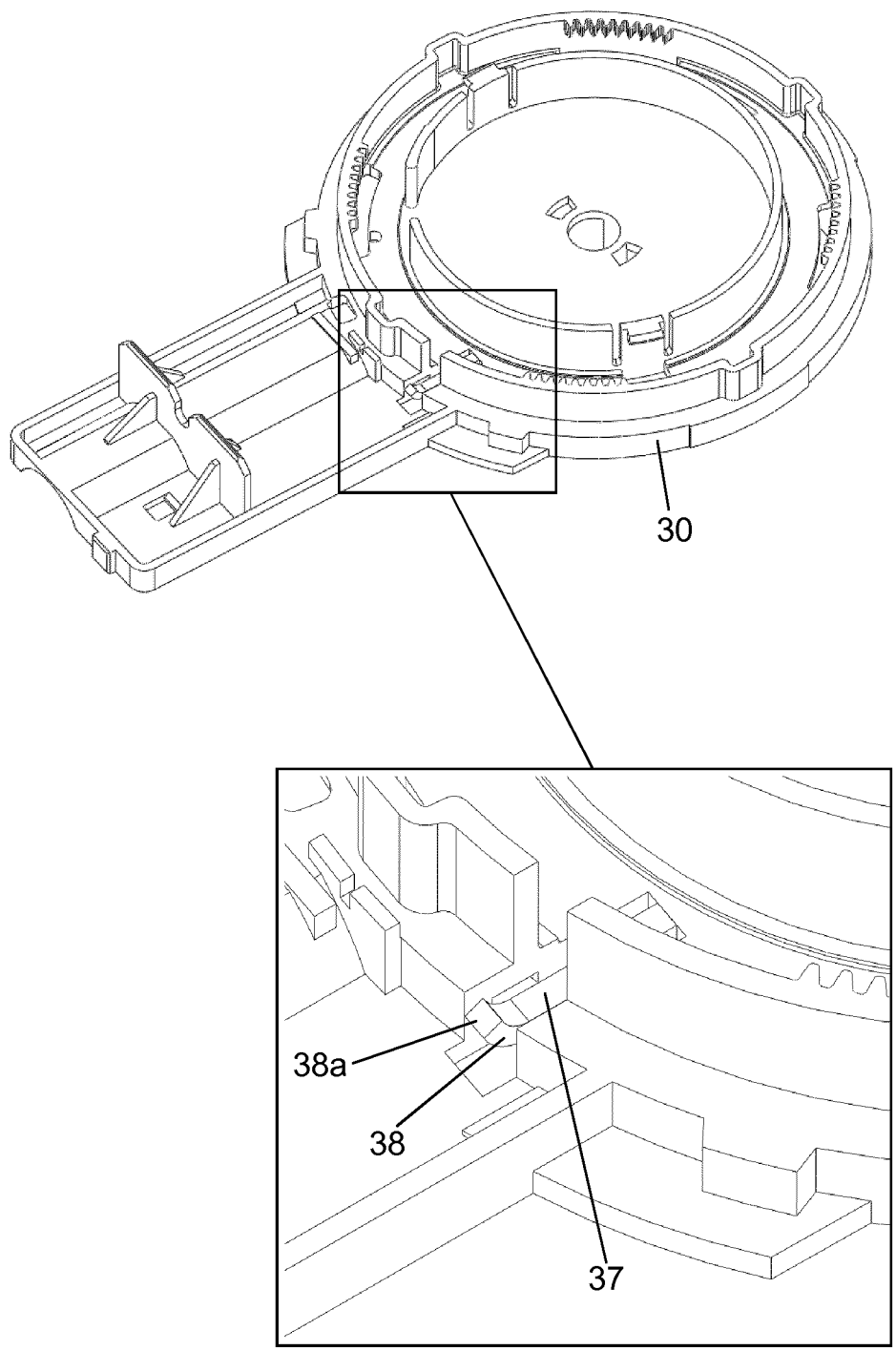
FIG. 13 a perspective view of the chassis (base element) of the embodiment of FIG. 1 with an enlarged portion.
Figure 14:
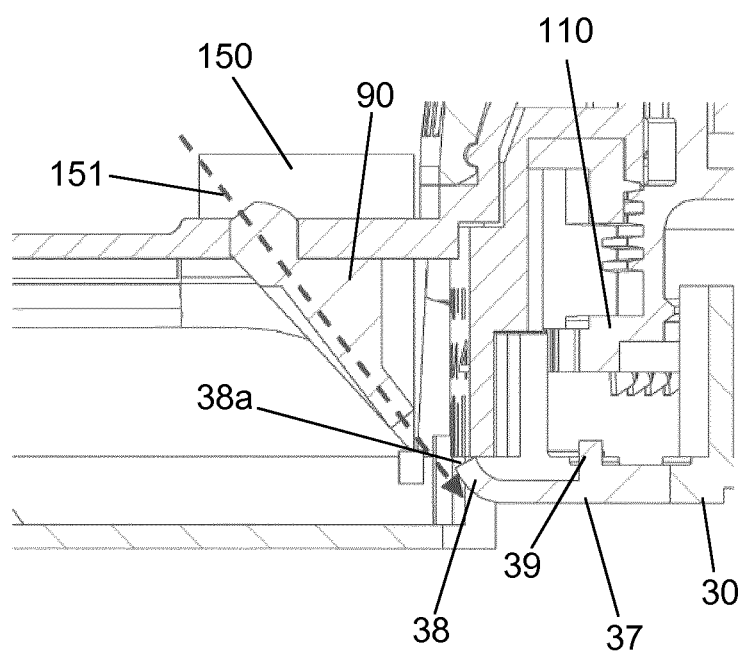
FIGS. 14-15 the operation of the determination unit in the dialing mode (FIG. 14) and the dispensing mode (FIG. 15) of the dosing mechanism of the embodiment of FIG. 1 in a part of a cut view.

FIG. 11 shows the inventive dosing mechanism of the drug delivery device 1 (see FIG. 1) with which the dialing mode can be distinguished from the dispensing mode in detail. The chassis 30 comprises at its lower surface, a lever arm 37 which is in its horizontal first position in FIGS. 11, 13 and 14. The the dosing mechanism is in the dialing mode when the lever arm 37 is in its horizontal first position. Preferably, the lever arm 37 is a flexible lever making up part of the chassis 30 with no hinge. Alternatively, the lever arm 37 may be coupled to the chassis 30 via a hinge. The flexible lever arm 37 with no hinge deflects under the load from the drive gear 110 and springs back to its horizontal level (first position) when the drive gear 110 does not provide any load to the lever arm 37. On its upper surface, the lever arm 37 comprises a protruding tip 38, which is slightly bent in an axial direction, forming a reflective surface 38*a* (see FIG. 13). Additionally, the lever arm 37 comprises an upper protrusion 39 projecting from the upper side of the lever arm 37 in the axial direction (see axis 117 in FIG. 10*a*).

FIG. 11 further shows the first module (electronic module) 150 which is releasably attached to the housing of the dosing mechanism or drug delivery device by a snap fit connection for example (not shown) covering the prism 90. The first module 150 comprises a determination unit with a proximity sensor (not shown) with a lighting element (not shown), for example an infrared LED. The determination unit comprises a data processing unit, e.g. a microprocessor. In the dialing mode shown in FIGS. 11 and 14 the lever arm 37 is in its first position such that the protruding tip 38 of the lever arm is in its first position, too. The protruding tip 38 comprises a reflective surface 38*a*.

Figure 15:
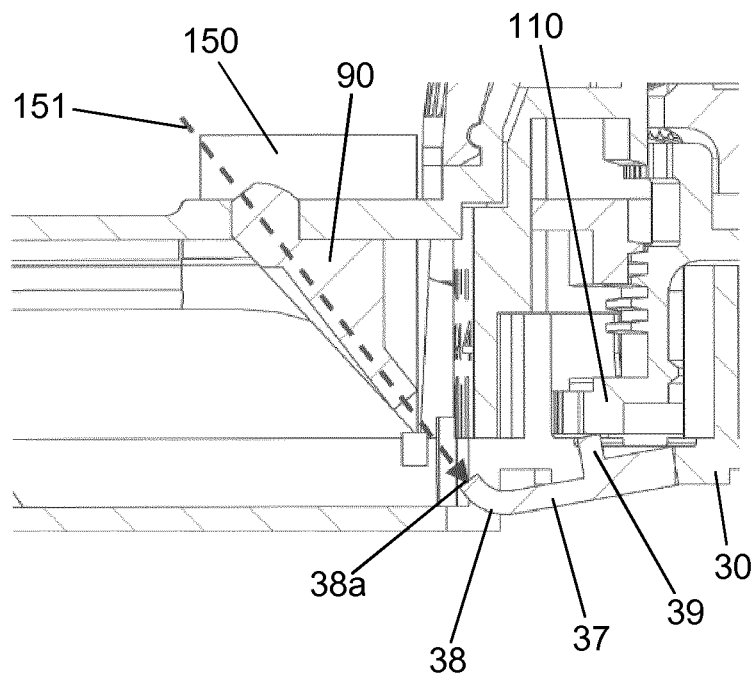

When the user has dialed the user settable dose the user is going to dispense the dose by pressing the dose button 40. This causes the drive gear 110 as described above to move axially and to disengage from the chassis 30 by moving it out of engagement with the chassis teeth enabling the drive spring 130 to release its stored energy and dispense the dose. Thereby, the lever arm 37 is moved into a second position caused by the load of the lower side of the drive gear 110 to an upper protrusion 39 of the lever arm 37 and bending it. The light being depicted in FIGS. 14 and 15 by a dashed line 151 impinges at the reflective surface (front face) 38*a* of the protruding tip 38 of the lever arm 37 as shown in FIG. 15. Then, the determination unit of the first module 150 detects higher back reflection of the light to the proximity sensor and hence judges that the dosing mechanism or drug delivery device is in the dispensing mode.

Thereby, the determination unit is able to differentiate between the dialing and dispensing modes and the doses dialed or dispensed. As shown in FIGS. 11 to 15 the lever arm 37 is bent by providing an axial load by the drive gear 110 to the protrusion 39 at the upper side of the lever arm 37. Alternatively, the drive gear 110 may have a protrusion at its lower side with which the lever arm 37 (without protrusion) may be pressed when the drive gear 110 is in its lower most position.

Further, the first module 150 may comprise a camera with which the magnified marking (numbering) 107 of the number wheel 100 is read. The dialed dose may then be displayed at a display (not shown) provided by the first module 150 at its upper side facilitating further enlargement of the marking in order to easy reading, in particular for vision impaired people.

Figure 16:
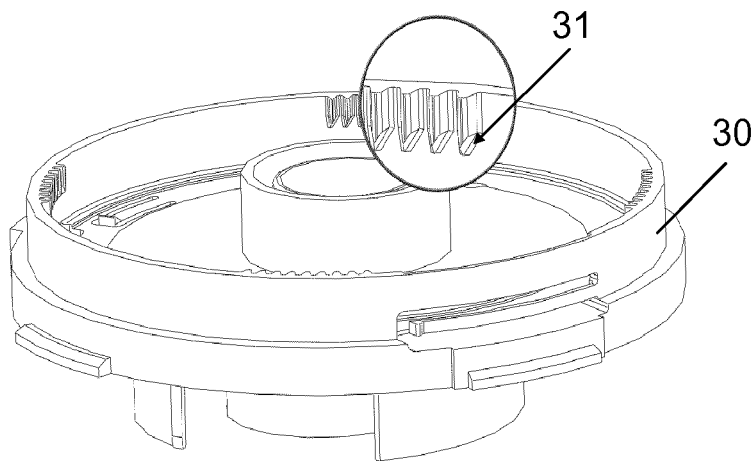
FIG. 16 a perspective view of the chassis (base element) in accordance with a third embodiment of the dosing mechanism.

In FIG. 16, a further embodiment is shown in which the spline teeth on the chassis are angled or have an angled face on their lower surface so that when the button 40 is released, the re-engagement of the spline teeth 31 fractionally backwinds the drive gear 110 thereby removing the engagement of the number wheel 100 to the zero dose stop abutment. Alternatively, the angled spline teeth may be provided on the dial gear 110. The angled feature removes the effect of clearances in the mechanism (for example due to tolerances). Clearances within the mechanism could cause the number wheel zero dose stop to no longer restrain the mechanism and instead the restraint would return to the splines between the drive gear and the chassis. This would undesirably lead to slight advancement of the piston rod and medicament dispense when the device is dialed for the subsequent dose.

Figure 17A:
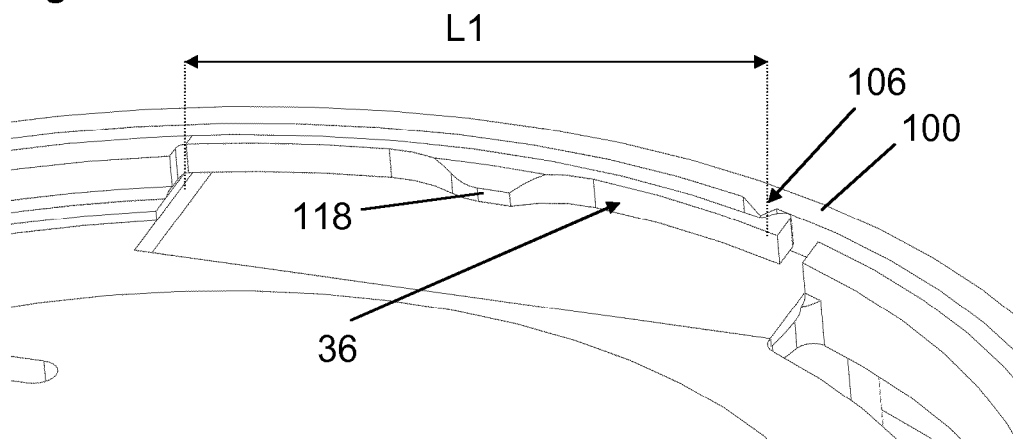
FIGS. 17a-b parts of the dosing mechanism in accordance with a fourth embodiment in a perspective view.
Figure 17B:
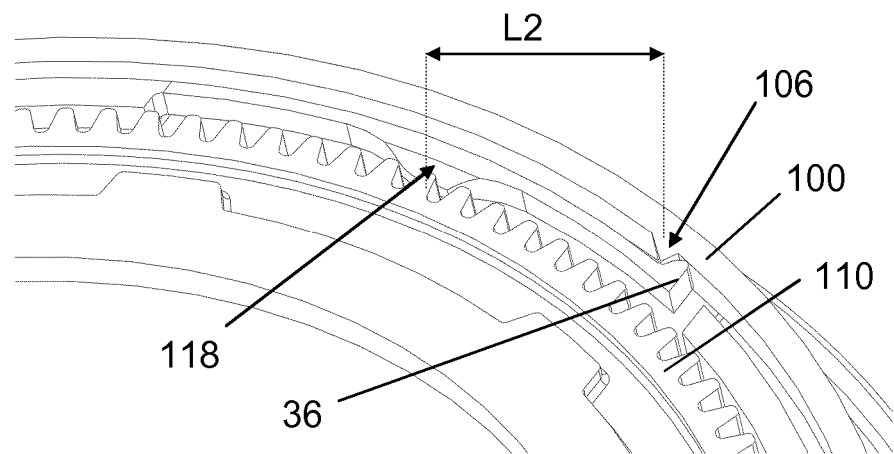

In FIGS. 17a and 17b a mechanism to indicate the end of dose is shown. The end of dose mechanism produces an audible click at the end of dose when the mechanism reaches its zero position. The click is created by interaction between a flexible clicker arm 36 on the chassis 30, the drive gear 110 and the number wheel 100. The volume of the click increases during dose delivery and is likely to be masked by the dial clicker when the user dials the device to or from zero. With respect to FIG. 17a, during dialing, the button 40 and the drive gear 110 are spaced axially away from the chassis 30, and the flexible clicker arm 36 is able to over-ride the protrusion 106 on an inner diameter of the number wheel 100 with minimum torque due to its large effective cantilever length L1 and therefore the volume of the audible click will be low. During dose delivery, when the button 40 and hence drive gear 110 are pushed axially towards the chassis 30, the inner surface of the clicker arm 36 contacts the drive gear 110, preferably by the protrusion 118, when the arm over-rides the bump feature or protrusion 106 of the number wheel 100. This contact with the drive gear 110 reduces the effective length of the clicker arm to L2 (FIG. 17b), thereby increasing its stiffness which leads to an increase in the volume of the audible click produced when the dose returns to zero.

Figure 18:
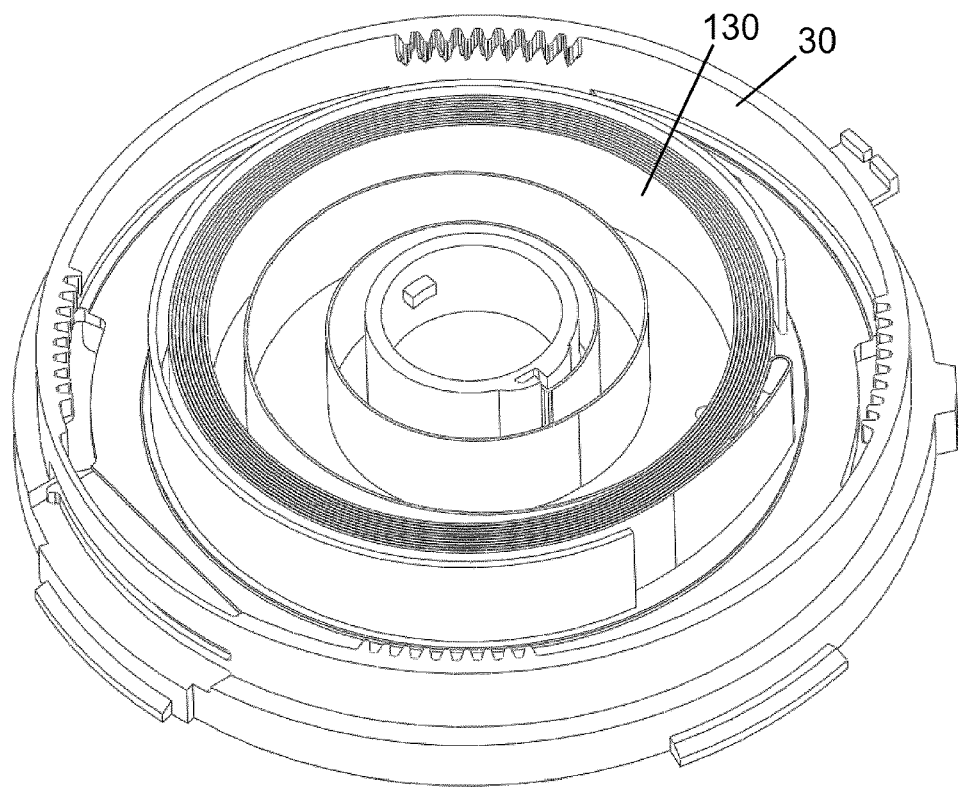
FIG. 18 parts of the dosing mechanism in accordance with a fifth embodiment in a perspective view.

Instead of a torsion spring, a power spring may be assembled. FIG. 18 is a perspective view of the device with a power spring fitted on the chassis. When using a torsion spring as the drive spring 130, the end-form of the spring can be fixed to the drive gear that moves axially when the button is pressed. The small amount of button travel and hence axial travel of drive gear 110 does not have a significant effect on the performance of the torsion spring. However, in particular when using a power spring, it may be beneficial that the inner end-form of the spring does not move axially with the drive gear. To implement this feature, another embodiment includes a drive gear that is split into two components that are rotationally fixed but that can move axially relative to each other.

Figure 19:
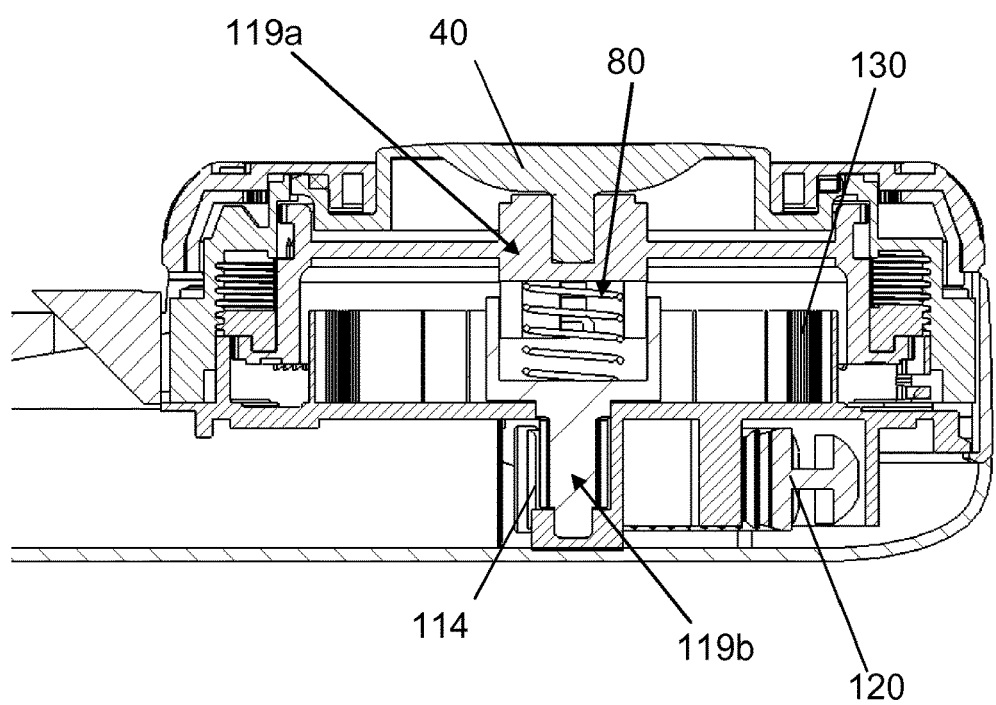
FIG. 19 parts of the dosing mechanism in accordance with a sixth embodiment in a cut view.

The embodiment shown in FIG. 19 includes a drive gear that includes two separate components that are rotationally fixed and axially movable relative to each other by spline engagement. The upper first drive gear component 119a constitutes the engagement section with the number wheel 100 and is also urged by the button 40 in downward direction during dispense. On a central section on the underside of the first drive gear component 119a, the protruding section of the first drive gear component 119a is received in an opening of the lower second drive gear component 119b. The components 119a and 119b interface by way of a spline connection formed on the outer diameter of the protruding section and on an inner diameter of the receiving section (opening) so that relative axial movement is possible like a telescope but relative rotation between the first drive gear component 119a and the second drive gear component 119b is prevented. The trigger spring 80 is arranged in said opening between the first drive gear component 119a and the second drive gear component 119b.

The lower component 119b does not move axially and secures the inner leg of the power spring 130. It also contains the pinion 114 that drives the flexible piston rod 120. The upper drive gear component 119a moves axially with the button travel relative to the second drive gear component 119b and interfaces with the number wheel 100 and the last dose nut 60. Alternatively, the pinion 114 may be part of an arbor that constitutes the second component. The two parts 119a and 119b are biased apart by the trigger spring 80, which also gives the advantage that during dose delivery, since both components are rotating together, the spring does not add any frictional losses that the drive spring 130 must overcome. When the button is actuated, which means that the button 40 is moved in downward direction so that the clutch between the drive gear 110 and the number wheel 100 is released, the trigger spring 80 is compressed.

Figure 20:
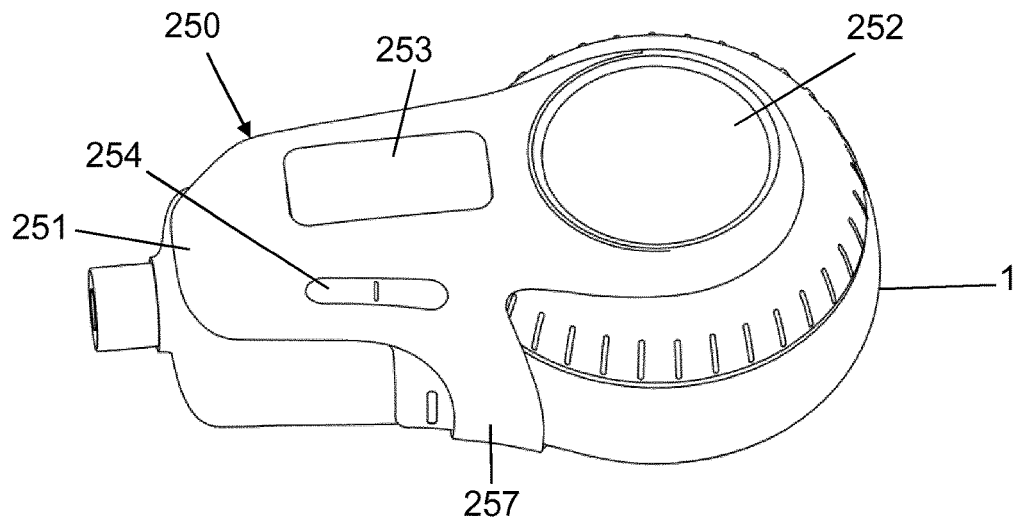
FIG. 20-22 a drug delivery device with a dosing mechanism according to a seventh embodiment in a perspective side view without cap, with cap and in an exploded view.
Figure 21:
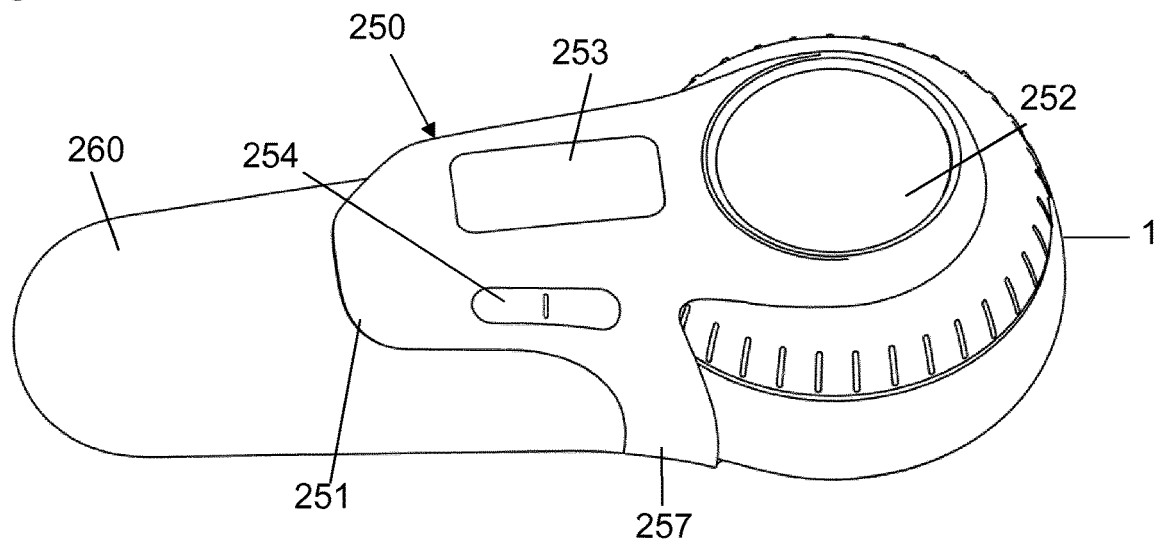
Figure 22:
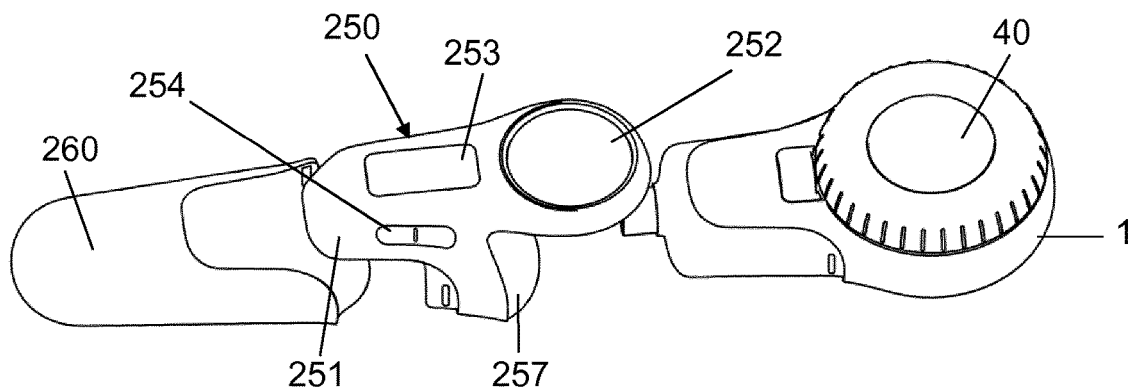

FIGS. 20 to 22 shows another embodiment in which the first module 150 is replaced by a second module 250 which is releasably attached to the upper casework 13 and the lower casework 14 of the drug delivery device 1. The second module 250 comprises a housing 251, a dose button 252, a display 253 and a module button 254. The housing 251 of the module 250 forms a loop 257. When attached to the drug delivery device 1 the housing 251 covers the dose button 40 of the drug delivery device 1 and prism 90 showing the printed numbers of the number wheel 100.

The dose button 252 interacts with the dose button 40 of the drug delivery device 1. In order to dispense a dose, the user depresses the dose button 252 of the second module 250 which leads to depression of the dose of button 40 of the drug delivery device 1 as the dose button 252 of the second module 250 is accommodated just above the dose button 40 of the drug delivery device 1 contacting and fully covering it.

The second module 250 is assembled axially from part of the drug delivery device 1 containing the cartridge 140 and cartridge holder 20. The distal end of the drug delivery device 1 is inserted into the free space formed by the loop 257 of the housing 251 in axial direction (see FIG. 22) and connected to the drug delivery device 1 by a snap-fit connection. Also in axial direction a cap 260 is attached to the distal end of the second module 250 and attached to it by another snap-fit connection.

The second module 250 comprises within the housing 251 a battery (not shown), the display 253, for example an LCD display, a determining unit comprising a 2-D sensor (not shown), a lens (not shown), a LED (not shown), and a light pipe (not shown).

The second module 250 shows the dialed dose on its display 253 using the lens and the prism 90. Therefor prism 90 and the lens focus the image shown on the number wheel 100 of the drug delivery device 1 at the 2-D sensor of the determination unit. The determination unit then performs number recognition in order to determine the dialed dose volume. The determined dialed dose volume is then displayed at the display 253.

The LED and the light pipe facilitate illumination of the protruding tip 38 of the lever arm 37 and the illumination of the number wheel 100. Thereby it is ensured that a clear image is captured by the 2-D sensor.

Figure 23:
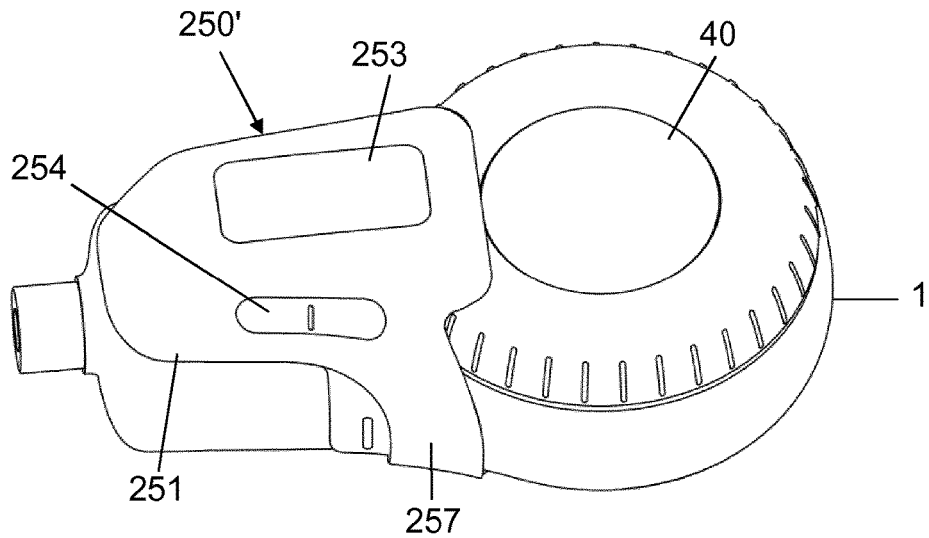
FIG. 23-25 a drug delivery device with a dosing mechanism according to an eighth embodiment in a perspective side view without cap, with cap and in an exploded view.
Figure 24:
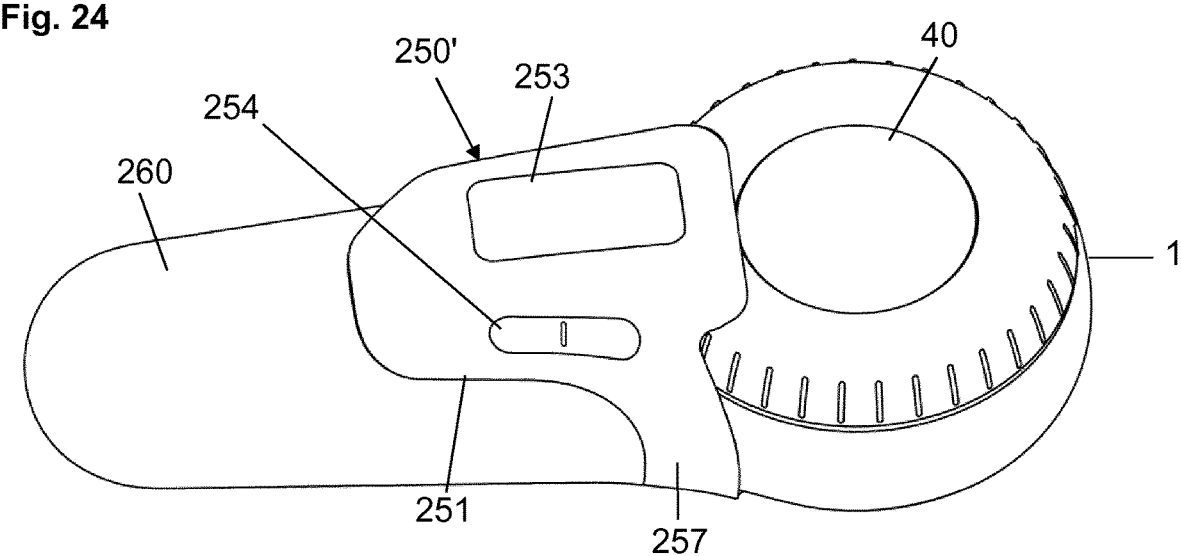
Figure 25:
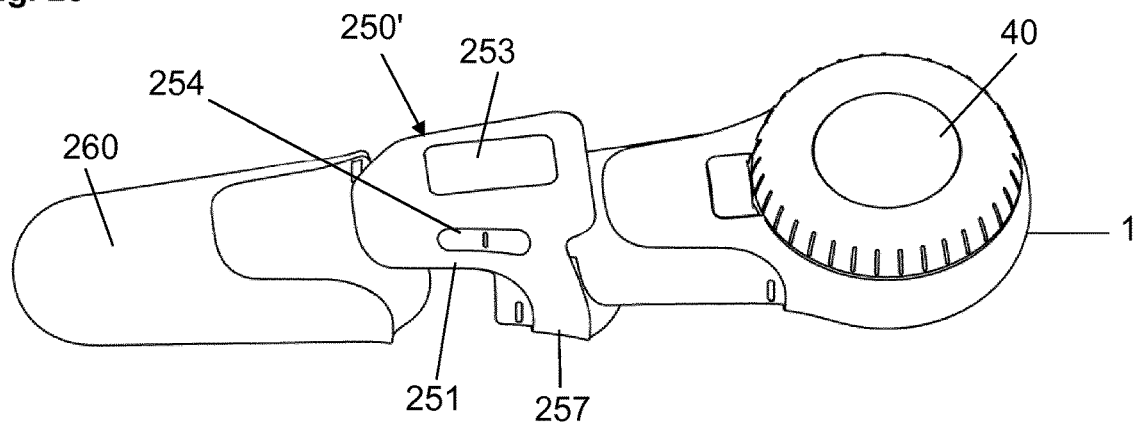

FIGS. 23 to 25 shows another embodiment in which the module 250 according to the second embodiment is replaced by a third module 250'. This third module 250' differs from the second module 250 therein that it has no dose button. Accordingly, the dose button 40 of the drug delivery device 1 is not covered by the third module 250'. The remaining parts and functions of the third module 250' are similar to the second module 250.

REFERENCE NUMERALS

1 drug delivery device
10 body (casework)
13 upper casework
14 lower casework
20 cartridge holder
30 chassis (base element)
31 spline teeth
36 clicker arm
37 lever arm
38 protruding tip of the lever arm 37
38*a* reflective surface
39 protrusion
40 dose button
42 spline/tooth features
43 spline/tooth features
50 dial member (dose setting member)
51 dial cover
52 spline/tooth features
54 dial clicker
55 dial clicker
60 last dose nut
62 outer thread
64 splined interface
80 trigger spring
90 prism
100 number wheel (setting element)
101 maximum dose stop
102 zero dose stop
103 spline/tooth features
104 spline/tooth features
105 end stop
106 protrusion
107 markings
110 drive gear
111 spline teeth
112 helical teeth
113 spline teeth
114 pinion
117 axis of rotation of drive gear
118 protrusion
119*a* first drive gear component
119*b* second drive gear component
120 flexible piston rod
121 segment (rigid rod piece)
122 hinge
123 rack teeth
130 drive spring
140 cartridge
150 first module
151 light beam
250 second module
250' third module
251 housing
252 dose button
253 display
254 button
257 loop
260 cap

The invention claimed is:

1. A dosing mechanism for use in a drug delivery device having a dialing mode and a dispensing mode, wherein the dosing mechanism comprises:
    a dose button,
    a housing, and
    a determination unit,
    wherein the dose button is activatable by a user for dose dispense causing displacement of a tip of a lever arm connected to the housing from a first position to a second position,
    wherein the lever arm is biased against displacement from the first position to the second position,
    wherein the determination unit comprises a proximity sensor configured to detect the tip of the lever arm in the second position using electromagnetic radiation provided by a lighting element, and the determination unit is configured to determine that the dosing mechanism is in the dispensing mode when the tip of the lever arm is detected by the proximity sensor.

2. The dosing mechanism according to claim 1, wherein the dosing mechanism comprises a transparent prism guiding the electromagnetic radiation from the proximity sensor of the determination unit to the tip of the lever arm.

3. The dosing mechanism according to claim 1, wherein the determination unit comprises a display which is adapted to visually and/or audibly indicate whether the dosing mechanism is in the dialing mode or in the dispensing mode.

4. The dosing mechanism according to claim 1, wherein the determination unit comprises a sensor for reading a dialed dose and/or a dispensed dose.

5. The dosing mechanism according to claim 4, wherein the sensor for reading the dialed dose and/or the dispensed dose is a camera.

6. The dosing mechanism according to claim 4, wherein the determination unit comprises a storage unit storing the read dialed doses or the read dispensed doses.

7. The dosing mechanism according to claim 4, wherein the determination unit comprises a display which is adapted to visually and/or audibly indicate the read dialed dose and/or the read dispensed dose.

8. The dosing mechanism according to claim 1, wherein the dosing mechanism comprises a drive gear coupled to the dose button, wherein activation of the dose button moves the dose button in an axial direction relative to the housing, thereby moving the drive gear in the axial direction relative to the housing which causes displacement of the tip of the lever arm from the first position to the second position.

9. The dosing mechanism according to claim 1, wherein the determination unit comprises a data processing unit.

10. A drug delivery device comprising a dosing mechanism comprising:
a dose button,
a housing, and
a determination unit,
wherein the dose button is activatable by a user for dose dispense causing displacement of a tip of a lever arm connected to the housing from a first position to a second position,
wherein the lever arm is biased against displacement from the first position to the second position;
wherein the determination unit comprises a proximity sensor configured to detect the tip of the lever arm in the second position using electromagnetic radiation provided by a lighting element, and the determination unit is configured to determine that the dosing mechanism is in a dispensing mode when the tip of the lever arm is detected by the proximity sensor.

11. The drug delivery device of claim 10, wherein the drug delivery device contains a medicament.

12. An assembly comprising:
a dosing mechanism comprising:
a dose button,
a housing and; and
a determination unit,
wherein the dose button is activatable by a user for dose dispense causing displacement of a tip of a lever arm connected to the housing from a first position to a second position,
wherein the lever arm is biased against displacement from the first position to the second position;
wherein the determination unit comprises a proximity sensor configured to detect the tip of the lever arm in the second position using electromagnetic radiation provided by a lighting element, and the determination unit is configured to determine that the dosing mechanism is in a dispensing mode when the tip of the lever arm is detected by the proximity sensor,
wherein the determination unit is accommodated within a separate module that is releasably attached to the housing of the dosing mechanism.

13. An assembly comprising
a drug delivery device comprising a dosing mechanism, the dosing mechanism comprising:
a dose button,
a housing, and
a determination unit,
wherein the dose button is activatable by a user for dose dispense causing displacement of a tip of a lever arm connected to the housing from a first position to a second position,
wherein the lever arm is biased against displacement from the first position to the second position,
wherein the determination unit comprises a proximity sensor configured to detect the tip of the lever arm in the second position using electromagnetic radiation provided by a lighting element, and the determination unit is configured to determine that the dosing mechanism is in a dispensing mode when the tip of the lever arm is detected by the proximity sensor,
wherein the determination unit is accommodated within a separate module that is releasably attached to the housing of the drug delivery device.

14. The drug delivery device of claim 13, wherein the drug delivery device contains a medicament.

* * * * *

UNITED STATES PATENT AND TRADEMARK OFFICE
CERTIFICATE OF CORRECTION

| | |
|---|---|
| PATENT NO. | : 10,758,680 B2 |
| APPLICATION NO. | : 15/568106 |
| DATED | : September 1, 2020 |
| INVENTOR(S) | : Samuel Keir Steel et al. |

Page 1 of 1

It is certified that error appears in the above-identified patent and that said Letters Patent is hereby corrected as shown below:

On the Title Page

Column 1 item (72), Line 7 (approx.), delete "Mickelton" and insert -- Mickleton --

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*